US006761532B2

(12) United States Patent
Capone et al.

(10) Patent No.: US 6,761,532 B2
(45) Date of Patent: Jul. 13, 2004

(54) TOUCH DOWN OF BLOOD PUMP IMPELLERS

(75) Inventors: Christopher D. Capone, Pittsburgh, PA (US); Ruey C. Dempsey, Greensburg, PA (US); Marlin S. Heilman, Sarver, PA (US); Steve A. Kolenik, Leechburg, PA (US); Daniel R. Moore, Gibsonia, PA (US); Carl M. Parisi, Kittanning, PA (US); Edward K. Prem, Allison Park, PA (US); Richard A. Sofranko, Pittsburgh, PA (US); David C. Borzelleca, Wexford, PA (US); Greg Burgreen, Bakerstown, PA (US); John A. Holmes, Wexford, PA (US); Zhongjun Wu, Wexford, PA (US); Ralph Scott Hebbert, Wexford, PA (US); James Antaki, Allison Park, PA (US)

(73) Assignee: Vascor, Inc., Pittsburgh, PA (US)

( * ) Notice: Subject to any disclaimer, the term of this patent is extended or adjusted under 35 U.S.C. 154(b) by 0 days.

(21) Appl. No.: 10/097,731

(22) Filed: Mar. 14, 2002

(65) Prior Publication Data

US 2003/0021683 A1 Jan. 30, 2003

Related U.S. Application Data

(60) Provisional application No. 60/275,732, filed on Mar. 14, 2001.

(51) Int. Cl.$^7$ ................................................ F04D 7/00

(52) U.S. Cl. ................... 415/900; 415/200; 416/170 R; 417/50

(58) Field of Search ........................... 415/900, 211.2, 415/200, 196, 173.1, 219.1, 221, 173.4; 416/170 R, 241 R; 417/50, 423.1

(56) References Cited

U.S. PATENT DOCUMENTS

| 4,382,199 | A | * | 5/1983 | Isaacson .................... 416/111 |
| 4,688,998 | A | | 8/1987 | Olsen et al. |
| 4,779,614 | A | * | 10/1988 | Moise ........................ 415/900 |
| 4,944,748 | A | | 7/1990 | Bramm et al. |
| 5,399,074 | A | * | 3/1995 | Nose et al. ................. 415/900 |
| 5,601,418 | A | * | 2/1997 | Ohara et al. ............... 415/900 |
| 6,050,975 | A | | 4/2000 | Poirier |
| 6,227,797 | B1 | | 5/2001 | Watterson et al. |
| 6,234,772 | B1 | * | 5/2001 | Wampler et al. ........... 415/900 |
| 6,250,880 | B1 | | 6/2001 | Woodard et al. |

* cited by examiner

Primary Examiner—Edward K. Look
Assistant Examiner—Igor Kershteyn
(74) Attorney, Agent, or Firm—Buchanan Ingersoll, P.C.

(57) ABSTRACT

A blood pump having rotor and/or stator touch down zones to prevent pump failure or hemolysis which can occur if the rotor comes into contact with the stator due to power failure or mechanical shock. The touch down zones can include forming, or coating, portions of adjacent surfaces of the stator and rotor which can come into contact if a rotor touch down occurs. The materials used to form or coat the touch down zones can have properties which ensure that no consequential damage to the contacting surfaces occurs.

8 Claims, 2 Drawing Sheets

TOUCH DOWN OF BLOOD PUMP IMPELLERS

CROSS REFERENCE TO RELATED APPLICATION

This application is based on U.S. Provisional Patent Application Serial No. 60/275,732, filed Mar. 14, 2001.

BACKGROUND OF THE INVENTION

The invention relates generally to blood pumps of the type in which a rotor, having impeller blades, is supported by magnetic bearings within a stator, and more particularly to preventing pump failure or hemolysis if the rotor should come into contact with the stator.

The number of donor hearts needed for persons having advanced heart failure has not decreased and consequently the need for a long-term alternative to heart transplantation remains. A fully implantable blood pump and system which is smaller than presently available systems and has the high reliability required for long term implantation would be a solution. To address this need, a variety of continuous flow blood pumps have recently been developed to address these requirements.

Continuous flow pumps generally have a rotor portion that has impeller blades for the pumping of blood and a surrounding stator which has features that mechanically support and turn the rotor to generate flow via the impeller blades. Some of these pumps have a mechanical bearing to support the rotor while others support the rotor in part or whole using a magnetic suspension system. Pumps which have mechanical bearings have the potential to cause hemolysis (blood damage) due to mechanical trauma or to heat generation, both of which are induced by the contact regions of the mechanical bearing. Some pumps employ a hydrodynamic bearing with the blood as the liquid portion of the bearing. Although much work has been done to determine the time duration and shear stress level at which hemolysis occurs, this type of rotor support has unknown long-term effects on blood. Pumps having magnetic suspension have the advantage of rotor-stator interaction that doesn't require contact or the extremely close tolerance between the rotor and stator of a hydrodynamic bearing, both of which induce mechanical trauma. However, one limitation of magnetic suspension is the control of the rotor during power failure or excessive mechanical shock to the blood pump. In these instances, the rotor may crash into the stator and cause surface damage to both components. In addition, most blood pump rotors use impeller blades for the pumping of blood. The blades are typically thin and consequently provide a small surface area for contact between the rotor and stator. The small surface area provided by the blade tips increases the likelihood of local surface damage. A larger surface area is better than a smaller one since the transfer of energy between the impacting components is spread out to a greater extent and consequently the surface damage will be less. Regardless of the size of the contact area, the touch down event can cause hemolysis and/or damage (scratch or gouge) the contacting surfaces of the rotor and/or stator which may subsequently cause thrombosis (blood clot) by providing a crack or crevice for the blood to begin depositing cells or other blood products.

One example of a blood pump in which the rotor is entirely supported by magnetic bearings is described in U.S. Pat. No. 4,688,998. When the operation of this blood pump is halted due to a power failure, the rotor shifts toward the inlet of the blood pump to block the backflow of blood through the blood pump. A portion of the rotor, referred to as the valve body, will contact a region of the stator, referred to as the valve seat, during power failure. No provision is made to have the rotor and stator portions designed to tolerate repeated impacts without damage to the blood contacting surfaces. This embodiment is again described in U.S. Pat. No. 4,944,748, which discloses additional embodiments of blood pumps that have magnetically suspended rotors. These embodiments likewise have no unique features for the tolerance of contact between the rotor and stator.

Another type of magnetically suspended blood pump is described in U.S. Pat. No. 6,050,975. This blood pump is designed to have a textured blood-contacting surface that promotes the growth of a biologic lining from the passing blood. Although this technique has been shown to produce beneficial results from the standpoint of preventing unstable clot formation, contact between the rotor and stator due to a power failure would potentially break loose tissue from the textured surface. Consequently, this pump cannot tolerate rotor-stator contact without causing serious harm to the patient.

Generally, touch down events may be grouped into two categories: touch down due to power failure; or touch down due to mechanical shock. If a blood pump power failure occurs, the rotor may, in certain designs, be slammed into the stator by the un-powered and consequently unbalanced magnetic bearings. For a well designed blood pump, the chance of a power failure is highly unlikely. However, for the safety of the patient, the blood pump must be designed to survive and correctly function after such a catastrophic event.

In contrast to touch down caused by a power failure, touch down due to mechanical shock is more difficult to account for, given the difficulty to predict the shock loading a patient may see if they are involved in an accident. One important consideration for determining the required magnetic suspension strength is the capability of the magnetic suspension to withstand the mechanical shock loading from everyday activity. In addition, there are considerations regarding the natural frequency of the magnetic suspension as a function of impeller rotational speed. Both of these issues tend to encourage a stiff magnetic bearing for rotor suspension. A stiffer suspension will enable larger shock loads to be tolerated without touch down occurring. Unfortunately, a stiffer suspension can also result in higher touch down loading if a power failure occurs.

It should be noted that touch down resulting from a mechanical shock will normally occur for a brief time period, typically only for an instant. In contrast, touch down resulting from a power failure can potentially bring the rotor to a complete stop, since the magnets will hold the rotor in place while the rotational energy is dissipated.

Accordingly, there is a need for a blood pump designed to eliminate surface damage that can occur if the rotor should come into contact with the stator.

SUMMARY

A blood pump is provided according to the invention wherein portions of the rotor and/or stator are designed to eliminate surface damage if the rotor and stator should come into contact with each other. This can be accomplished generally by specially designing the portions of the rotor and stator which are likely to come into contact as a result of power failure or mechanical shock. In particular, likely touch down contact surfaces of the rotor and/or stator can be made from materials having properties such that generally even the highest touch down forces would not cause any surface damage. Alternatively, the geometry of the likely touch down contact surfaces of the rotor and/or stator can be designed such that the touch down forces are spread across the largest possible surface area to reduce the contact stresses. Moreover, a combination of the choice of materials and the design of the geometry of the likely touch down contact surfaces can be employed to achieve the desired results of eliminating surface damage in the event of rotor touch down against the stator.

Other details, objects, and advantages of the invention will become apparent from the following detailed description and the accompanying figures of certain embodiments thereof.

BRIEF DESCRIPTION OF THE DRAWING FIGURES

A more complete understanding of the invention can be obtained by considering the following detailed description in conjunction with the accompanying drawings, in which.

DETAILED DESCRIPTION

Figure 1:
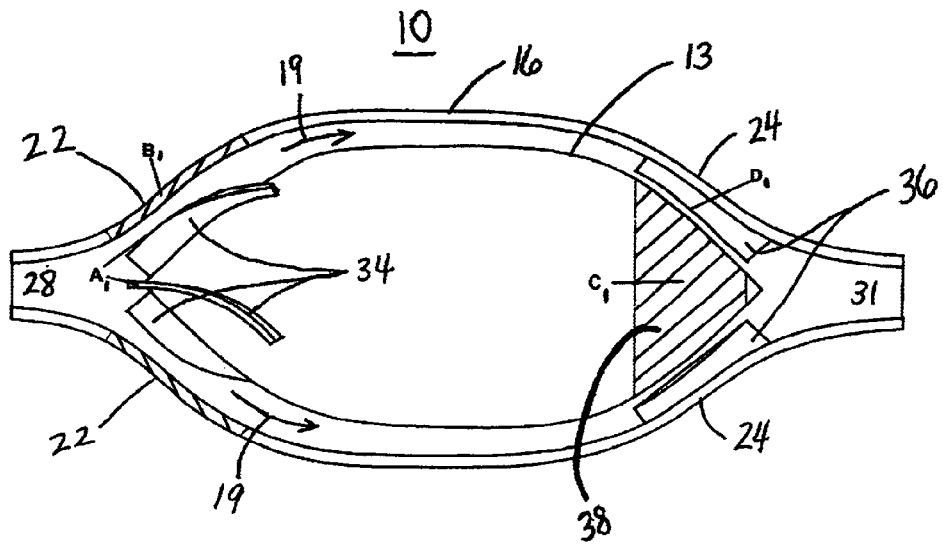
FIG. 1 is a side cross section view of an exemplary embodiment of an single gap axial flow blood pump according to the invention.

Referring now to the drawing figures, like reference numbers refer to similar parts throughout the several views. Except for FIG. 2, generally only the rotor and stator members of the blood pump are illustrated since it is those components which are pertinent to understanding the details of the invention. The invention is primarily concerned with adjacent regions of the rotor and stator which are most likely to come into contact with each other in the case of a rotor touch down event. In particular, as will be described in greater detail hereinafter, the material composition and geometry of such adjacent regions of the rotor and/or stator can be designed to generally eliminate any surface damage resulting from contact due to touch down events. The materials chosen can have properties such that touch down contact will not result in damage to the contacting rotor and stator surfaces. The geometry of the portions of the adjacent surfaces of the rotor and stator can be designed to spread the force of contact over a larger area, and can further be designed to simultaneously account for touch downs in both the axial and radial directions.

Figure 3:
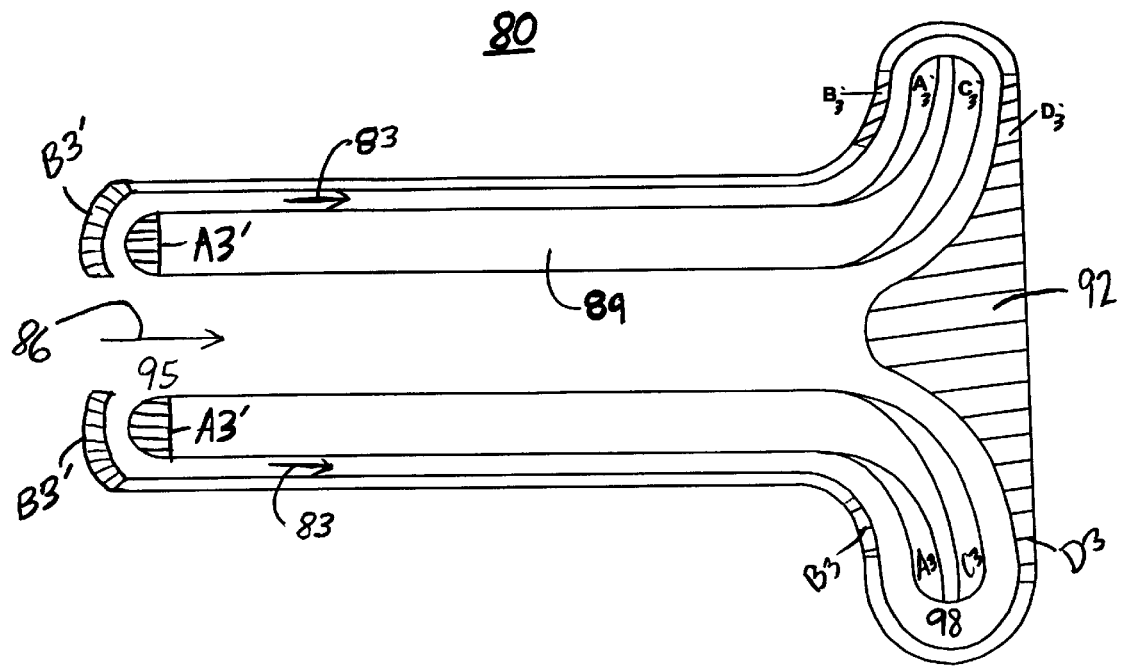
FIG. 3 is a side cross section view of an exemplary embodiment of a dual gap centrifugal blood pump according to the invention.
Figure 4:
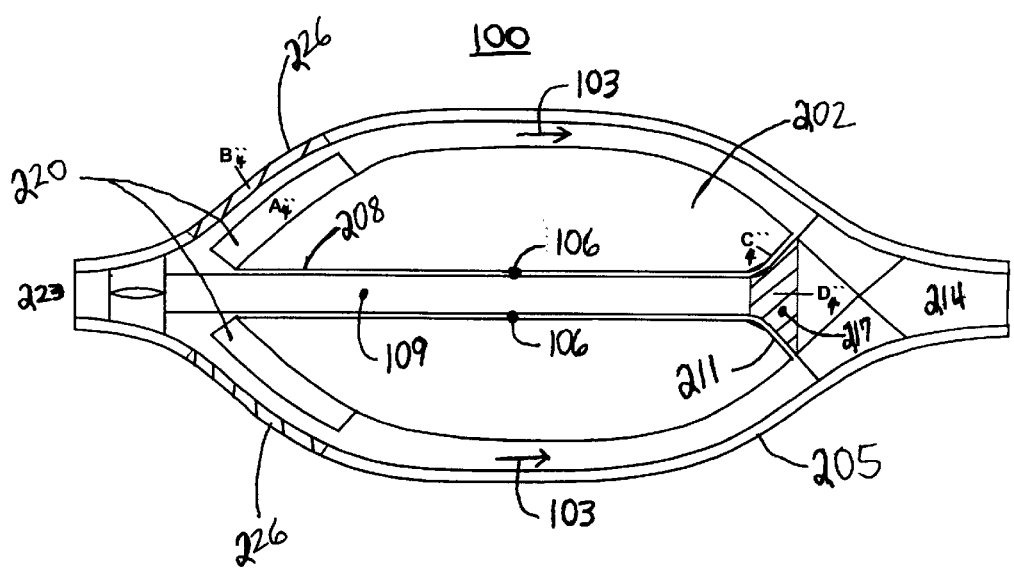
FIG. 4 is a side cross section view of an exemplary embodiment of a dual gap axial flow blood pump according to the invention.

In accordance with the foregoing, FIGS. 1, 3 and 4 are generally simplified depictions of blood pumps, showing a rotor housed within a stator, wherein portions of adjacent regions of the rotor and stator have "touch down zones." In each Figure, the rotor is magnetically suspended and rotated within the stator, although the details of the magnetic suspension and rotation system are not shown. In FIG. 1, the touch down zones are designated A1, B1, C1, and D1, wherein A1 designates a first, or fore, touch down zone portion of the rotor and B1 designates a corresponding fore touch down zone portion of the stator which, in the event of rotor touch down, will be contacted by touch down zone A1.

Similarly, C1 designates a second, or aft, touch down zone portion of the rotor, and D1 designates a corresponding aft touch down zone portion of the stator which, in the event of rotor touch down, will be contacted by touch down zone C1.

Figure 2:
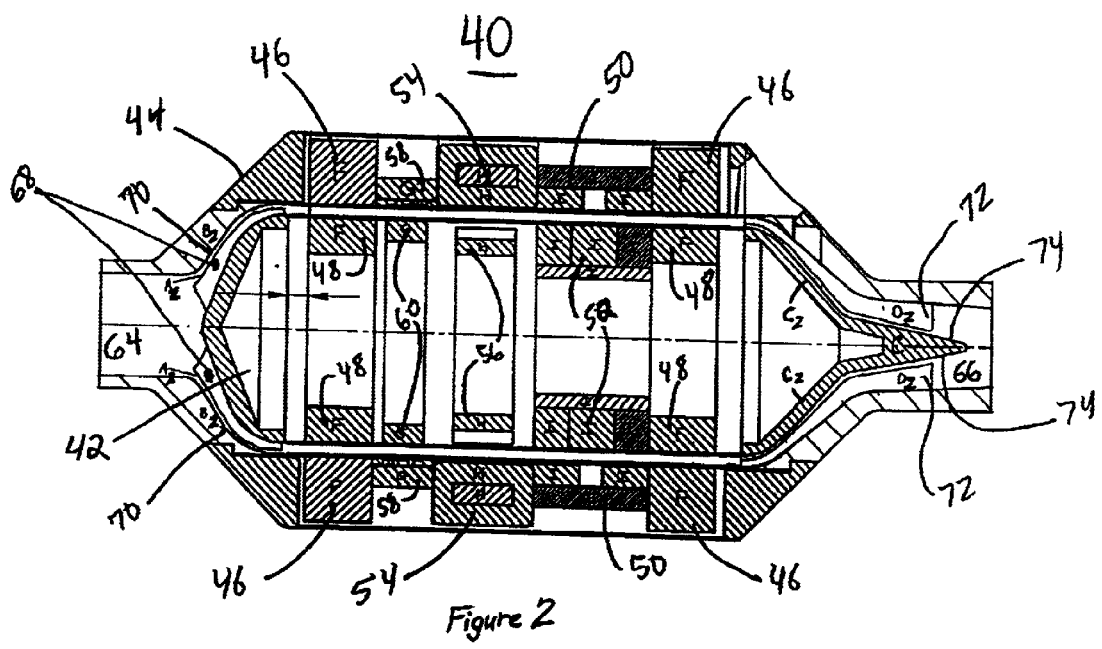
FIG. 2 is a view of a single gap axial flow pump similar to FIG. 1, except illustrating more details of such a pump.

The touch down zones of the various blood pump embodiments illustrated in FIGS. 2 through 4 are similarly labeled, in regard to fore and aft touch down zones of the rotor and stator. For example, in FIG. 2, touch down zones A2, B2, C2, and D2 correspond to touch down zones A1, B1, C1, and D1 in FIG. 1. Likewise, touch down zones A3, B3, C3 and D3 in FIG. 3, and touch down zones A4, B4, C4 and D4 in FIG. 4, each also correspond to touch down zones A1, B1, C1, and D1 in FIG. 1. In accordance with the invention, each of the touch down zones in any of FIGS. 1 through 4, on either the rotor or the stator, can be smooth or may have blades. However, adjacent touch down zones of the rotor and stator will generally be smooth-to-smooth or blade-to-smooth, but not blade-to-blade.

Referring now particularly to FIG. 1, a simplified drawing of an axial flow pump 10 is depicted showing only the rotor 13 magnetically supported within the stator 16. In this configuration, the blood pump has a single blood flow path 19. As shown, axial motion of the rotor 13 is restrained within the stator 16 by portions 22, 24 of the stator wall at inlet (fore) 28 and outlet (aft) 31 sides of the blood pump. Touch down zones A1-B1 are provided at the fore end 28 of the pump 10 and touch down zones C1–D1 are provided at the aft end 31. In the pump inlet 28 region, impeller blades 34 are provided on the rotor 13 which rotate in close proximity to the adjacent wall portion 22 of the stator. At the inlet side 28 of the pump 10, the tips of the impeller blades 34 constitute touch down zone A1 and the adjacent wall portion 22 of the stator 16 constitutes corresponding touch down zone B1. Due to the geometry of the impeller blades 34 and the stator wall portion 22, excessive axial motion of the rotor 13 towards the pump inlet 28 can result in touch down between zones A1 and B1.

Consideration must also be given for axial motion of the rotor 13 toward the pump outlet 31. In the pump inlet region 28, the bladed touch down zone A1, is on the rotor 13 whereas in the pump outlet region 31, the bladed touch down zone D1 is part of the stator 16. The blades 37 on the stator 16 can be inwardly pointing, which serves to straighten the flow of blood as it exits the pump outlet 31. Corresponding rotor touch down zone C1 constitutes the 40 portion of the rotor 13 surface adjacent the stator touch down zone D1. Although a particular configuration of the rotor 13 and stator 16 is shown, it is to be understood that other configurations can be designed by those skilled in the art.

Rotor touch down, is not limited to the axial direction, but can also occur in the radial direction. Moreover, a rotor touch down may have both axial and radial components. Consequently, at both the pump inlet 28 and pump outlet 31 regions, the touch down zones A1 through D1 can be designed to accommodate rotor touch down from radial or axial directions, or a combination thereof. This can be achieved by controlling the geometry of the fore and aft touch down zone portions of the rotor 13 and stator 16, and/or by forming the cooperating fore and aft touch down zones over a large surface area. In particular, this can be accomplished by making on or both touch adjacent down zone portions extend axially along the length of the rotor and/or stator sufficiently to ensure that a rotor touch down, from generally any direction, will result in contact between only the adjacent touch down zone portions. Thus, the rotor 13 can be constrained within the stator 16 both radially and axially, such as by bladed touch down zones A1 and D1 at the pump inlet 28 and by the smooth touch down zones B1 and C1 at the pump outlet 31.

At the pump inlet 28 area, the impeller blades 34, or the tips thereof, (touch down zone A1) and the adjacent portion 22 of the stator 16 wall (touch down zone B1) may be formed from, or coated to a sufficient thickness with, a variety of specially selected materials. The materials chosen for adjacent touch down zones can be generally categorized into three groups: hard surface to hard surface; soft surface to hard surface; or soft surface to soft surface. As an example, a hard surface on stator touch down zone B could be provided using pure titanium, an alloyed titanium, a crystalline-diamond-like coated pure or alloyed titanium, a titanium nitride coated pure or alloyed titanium, a graphitic-diamond-like coated pure or alloyed titanium, or a jewel, like sapphire. Likewise, the blade tips of touch down zone A may be a pure titanium, an alloyed titanium, a crystalline-diamond-like coated pure or alloyed titanium, a titanium nitride coated pure or alloyed titanium, a graphitic-diamond-like coated pure or alloyed titanium, or a jewel, like sapphire. Other hard materials like ceramics could also be used.

As for soft materials, PEEK (polyetheretherkeytone) is preferred, but any similar polymer, rubber, a combination thereof, or other relatively soft materials having similar properties, could also be used. The soft material could be used for either the impeller blades of touch down zone A1 or the stator touch down zone B1. The exact configuration of materials can depend on the particular application and related considerations. Additionally, other material combinations will also be apparent to those skilled in light of this disclosure.

Similar configurations as described above regarding materials for touch down zones A1 and B1 are also possible on the outlet end 31 of the blood pump 10 regarding touch down zones D1 and C1, respectively. The portion 40 of the rotor 13 at the pump outlet 31 can have a smooth touch down zone C1. The stator 16 blades 37 forming touch down zone D1 and the rotor 13 touch down zone C1 can have material selections/breakdowns as described above.

Referring now to FIG. 2, a presently preferred embodiment of a single gap axial flow blood pump 40 is shown, which can be similar to the blood pump 10 shown in FIG. 1, except that a more detailed illustration is provided, including details of the magnetic suspension and rotation systems. In particular, the rotor 42 can be supported radially within the stator 44 by cooperating magnetic radial bearing members 46, 48 on the rotor 42 and the stator 44, respectively. The rotor 42 can be magnetically supported in the axial direction by cooperating Lorentz force axial bearing members 50, 52 on the stator 44 and rotor 42, respectively. The rotor 42 can be rotated via magnetic drive members 54, 56 on the stator 44 and rotor 42 respectively. The magnetic drive members 54, 56 can comprise a toroidally wound motor. An axial position sensor can be also provided via cooperating stator 44 sensor portion 58 and rotor 42 sensor portion 60.

In the single gap axial flow pump 40, the rotor 42 can be entirely magnetically supported and rotated within the stator 44. Thus, as in the blood pump 10 shown in FIG. 1, axial movement of the rotor 42 can be restrained within the stator 44 by portions of the stator 44 at inlet (fore) 64 and outlet (aft) 66 sides of the blood pump 40 Therefore, touch down zones A2–B2 are provided at the pump inlet 64 and touch down zones C2–D2 are provided at the pump outlet 66. In the pump inlet 64 region, impeller blades 68 on the rotor 42 sweep in close proximity to the adjacent stator wall surface.

Thus, the impeller blades 68, or the tips thereof, can constitute touch down zone A2 and the adjacent portion of the stator wall can constitute adjacent touch down zone B2. Due to the geometry of touch down zones A2 and B2, excessive axial motion of the rotor 42 towards the pump inlet 64 will result in touch down between zones A2 and B2. Also like the blood pump 10 shown in FIG. 1, separate consideration is given for axial motion of the rotor 42 toward the pump outlet 66. At the pump outlet 66, blades 72 can be provided on the stator 44 to straighten the blood flow as it exits the pump 40. The blades 72 can be inwardly pointing, for the same reason explained in connection with FIG. 1. The flow straightening blades 72 can constitute aft touch down zone D2. The region of the rotor 42 adjacent the blades 72 can constitute touch down zone C2. Although a particular configuration of the rotor 42 and stator 44 is shown, it is to be understood that other configurations can be designed by those skilled in the art.

As described in connection with FIG. 1, there are likewise a number of different types of materials, and combinations of materials, for adjacent touch down zones which can be selected to eliminate damage that can result from rotor 42 touch down against the stator 44. In particular, the fore A2–B2 and aft C2–D2 touch down zones can be made of hard and/or soft materials, and various combinations thereof, depending on design requirements.

Referring now to FIGS. 3 and 4, other pump concepts which have touch down zones are depicted. In particular, FIG. 3 depicts a simplified illustration of a dual gap centrifugal pump 80, including a rotor 89 housed within a stator 92 and separated therefrom by a magnetic suspension gap 83. The magnetic suspension gap 83 forms a secondary blood flow path in addition to the main blood flow path 86. Provision of two gaps 83, 86 can enable provision of a narrower suspension gap 83 between the magnets of the bearing suspension system, which lowers the amount of energy required to suspend the pump rotor 89 radially within the stator 92. The touch down zones are labeled in a manner similar to that of the blood pump 10 shown in FIG. 1. Specifically, although the stator 92 touch down zones B3, and D3, are much closer to the rotor 89 touch down zones A3 and C3, they may still be defined as fore, A3–B3, and aft, C3–D3, touch down zones, respectively. Likewise, the fore touchdown zones can instead be situated closer to the inlet end of the blood pump. Zones A3' and B3' can be used as opposed to zones A3 and B3. Like the axial flow pump 10 shown in FIG. 1, there are a number of potential different types of materials, and combinations of material in adjacent touch down zones, which can be selected to eliminate damage from rotor touch down. The touch down zones A3 through D3, as well as A3' and B3', at the inlet (fore) 95 and outlet (aft) 98 ends of the rotor 89 and stator 92 can be made of hard and/or soft materials and various combinations thereof as described above in connection with FIG. 1, depending on the design requirements.

Referring now to FIG. 4, there is shown a simplified illustration of an axial flow blood pump 100 having primary 103 and secondary blood flow gaps 106, and in which there is provided a central shaft 109 which constrains a rotor 202 internally within a stator 205. The narrow secondary, i.e., magnetic suspension, gap 106 is the gap between an inner surface of a bore 208 through the center of the rotor 202 and an outer surface of the central shaft 109 which extends through the bore 208. The end 211 of the bore 208 at the outlet side 214 of the pump 100 can have an outwardly tapering opening, and the central shaft 109 can have a correspondingly tapering larger end 217, which serves to provide an axial support for the rotor 202. Blades 220 can be provided on the rotor 202 at the inlet side 223 of the pump 100 which cooperate with a portion 226 of the stator 205 to provide corresponding axial restraint on the inlet side 223 of the pump 100. As with the previously described embodiments of blood pumps 10, 80, the dual gap axial flow pump 100 can have fore A4–B4 and aft C4–D4 touch down zones. The fore touch down zones A4–B4 at the inlet 223 of the pump 100 includes rotor 202 touch down zone A4 and stator 205 touch down zone B4, and is very similar to the fore touch down zones A1–B1 at the inlet 28 of the single gap axial flow pump 10 shown in FIG. 1. However, the aft touch down zones C4–D4 at the outlet 214 of the pump 100 can be configured somewhat differently than the aft touch down zones C1–D1, owing to the central shaft 109 extending through the bore 208 in the rotor 202. In particular, the pump outlet 214 can have aft rotor touch down zone C4 provided on the inner surface of the bore 208, and particularly on the outwardly tapering end 211 of the bore 208. Aft stator touch down zone D4 can be provided on the correspondingly tapering larger end 217 of the central shaft 109, which is adjacent rotor touch down zone C4.

In the dual gap axial blood pump 100 shown, aft touch down zones C4–D4 can both be smooth surfaces. Moreover, as explained in connection with FIG. 3, there are a number of potential different types of materials, and combinations of material in adjacent touch down zones, which can be selected to eliminate damage from rotor touch down, as described in connection with FIG. 1. Thus, the fore and aft touch down zones of the rotor 202 and stator 205 can be made of hard and/or soft materials and various combinations thereof as described above in connection with FIG. 1, depending on design requirements.

In general, with any particular embodiment of a blood pump with touch down zones, a key factor to be considered is the geometric orientation of the touch down zone. The touch down zones, as shown in all of the drawing figures, can be configured such that the zones can simultaneously account for both axial and radial touch down. This can be accomplished through design of the specific geometry of the rotor and stator, particularly in the regions which are to be touch down zones. The size of the touch down zones can also affect this aspect of the invention, since the various touch down zone may need to extend sufficiently inwards from both the inlet and the outlet of the blood pump in order to accommodate radially directed touch downs, or a combination of radially and axially directed touch down events. Moreover, the size of the touch down zones can also be important in that a relatively large surface area can be desired, over which the force of touch down events can be spread. Spreading the force of touch down impact over a larger area will reduce imposed stresses and thereby lessen the likelihood of damage to either the rotor or the stator as a result of a touch down event.

Although certain embodiments of the invention have been described in detail, it will be appreciated by those skilled in the art that various modifications to those details could be developed in light of the overall teaching of the disclosure. Accordingly, the particular embodiments disclosed herein are intended to be illustrative only, and not limiting to the scope of the invention which should be awarded the full breadth of the following claims and any and all embodiments thereof.

What is claimed is:

1. A blood pump having inlet and outlet regions, said blood pump comprising:
    a. a stator having at least one of first and second contact portions adjacent at least one of said inlet and outlet regions, respectively;
    b. a rotor magnetically supported adjacent said stator for rotation relative thereto, said rotor having at least one of third and fourth contact portions adjacent said at least one of first and second contact portions, respectively;
    c. at least one of said first and second contact portions having properties resistant to damage resulting from potential touch down of said rotor against said stator;
    d. at least one of said third and fourth contact portions having properties resistant to damage resulting from potential touch down of said rotor against said stator; and
    e. wherein each of said first through fourth contact portions are at least one of titanium, alloyed titanium, ceramic, and a jewel.

2. The blood pump of claim 1 wherein said first through fourth contact portions are one of titanium and alloyed titanium, and further comprising said first through fourth contact portions having one of a crystalline-diamond-like coating, titanium nitride coating, and graphitic-diamond-like coating.

3. A blood pump having inlet and outlet regions, said blood pump comprising:
    a. a stator having at least one of first and second contact portions adjacent at least one of said inlet and outlet regions, respectively;
    b. a rotor magnetically supported adjacent said stator for rotation relative thereto, said rotor having at least one of third and fourth contact portions adjacent said at least one of first and second contact portions, respectively;
    c. at least one of said first and second contact portions having properties resistant to damage resulting from potential touch down of said rotor against said stator;
    d. at least one of said third and fourth contact portions having properties resistant to damage resulting from potential touch down of said rotor against said stator; and
    e. at least one of said first and third contact portions comprise blade members, and said blade members being a relatively soft material.

4. The blood pump of claim 3 further comprising at least one of said first and fourth contact portions adjacent said at least one of said second and third contact portions being a relatively hard material.

5. A blood pump having inlet and outlet regions, said blood pump comprising:
    a. a stator having at least one of first and second contact portions adjacent said outlet regions;
    b. a rotor magnetically supported adjacent said stator for rotation relative thereto, said rotor having at least one of third and fourth contact portions adjacent said at least one of first and second contact portions, respectively;
    c. at least one of said first and second contact portions having properties resistant to damage resulting from potential touch down of said rotor against said stator;
    d. at least one of said third and fourth contact portions having properties resistant to damage resulting from potential touch down of said rotor against said stator; and
    e. wherein each of said first through fourth contact portions are at least one of titanium, alloyed titanium, ceramic, and a jewel.

6. The blood pump of claim 5 wherein said first through fourth contact portions are one of titanium and alloyed titanium, and further comprising said first through fourth contact portions having one of a crystalline-diamond-like coating, titanium nitride coating, and graphitic-diamond-like coating.

7. A blood pump having inlet and outlet regions, said blood pump comprising:

a. a stator having at least one of first and second contact portions adjacent said outlet regions;

b. a rotor magnetically supported adjacent said stator for rotation relative thereto, said rotor having at least one of third and fourth contact portions adjacent said at least one of first and second contact portions, respectively;

c. at least one of said first and second contact portions having properties resistant to damage resulting from potential touch down of said rotor against said stator;

d. at least one of said third and fourth contact portions having properties resistant to damage resulting from potential touch down of said rotor against said stator; and e. at least one of said third and fourth contact portions comprise blade members, and said blade members being a relatively soft material.

8. The blood pump of claim 7 further comprising at least one of said first and second contact portions being a relatively hard material.

* * * * *